US010650927B2

(12) United States Patent
Are et al.

(10) Patent No.: US 10,650,927 B2
(45) Date of Patent: May 12, 2020

(54) MACHINE LEARNING CLINICAL DECISION SUPPORT SYSTEM FOR RISK CATEGORIZATION

(71) Applicant: CERNER INNOVATION, INC., Kansas City, KS (US)

(72) Inventors: Sasanka Are, Kansas City, MO (US); John Matthew Sugden, Lee's Summit, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 727 days.

(21) Appl. No.: 15/350,915

(22) Filed: Nov. 14, 2016

(65) Prior Publication Data

US 2017/0140114 A1   May 18, 2017

Related U.S. Application Data

(60) Provisional application No. 62/254,953, filed on Nov. 13, 2015.

(51) Int. Cl.
*G16H 50/30* (2018.01)
*G16H 50/20* (2018.01)
*G06N 20/00* (2019.01)
*G06N 5/00* (2006.01)
*G06N 20/20* (2019.01)

(52) U.S. Cl.
CPC ........... *G16H 50/20* (2018.01); *G06N 5/003* (2013.01); *G06N 20/00* (2019.01); *G06N 20/20* (2019.01)

(58) Field of Classification Search
CPC .............................. G16H 50/20; G16H 50/30
See application file for complete search history.

(56) References Cited

U.S. PATENT DOCUMENTS

| 5,799,101 | A * | 8/1998 | Lee ...................... G06K 9/6282 128/922 |
| 7,392,201 | B1 * | 6/2008 | Binns .................... G06F 19/328 600/300 |
| 7,685,000 | B1 * | 3/2010 | Petit ...................... G06F 19/328 705/2 |
| 7,853,456 | B2 |  12/2010 | Soto et al. |

(Continued)

OTHER PUBLICATIONS

Thorpe, K and Lever, J. Prevention: the answer to curbing chronically high health care costs. (2011) Available at: http://www.kaiserhealthnews.org/Columns/2011/May/052411thorpelever.aspx.

(Continued)

*Primary Examiner* — John A Pauls
(74) *Attorney, Agent, or Firm* — Shook, Hardy & Bacon L.L.P.

(57) ABSTRACT

Improved risk categorization is provided for clinical decision support and forecasting future health care spend. A risk index is provided that improves on other risk stratification models by synthesizing electronic medical records and health questionnaires with an individual patient's claim histories. Machine learning algorithms catalogue patients into distinct group clusters, based on risk which may be associated with annual health care spending, thereby enabling administrators to forecast future health care spending on the individual and population level.

18 Claims, 12 Drawing Sheets
(3 of 12 Drawing Sheet(s) Filed in Color)

(56) References Cited

U.S. PATENT DOCUMENTS

| | | | |
|---|---|---|---|
| 2005/0032066 A1* | 2/2005 | Heng | G16B 40/00 435/6.11 |
| 2009/0216558 A1* | 8/2009 | Reisman | G06F 19/328 705/3 |
| 2016/0078184 A1* | 3/2016 | Konerman | G06F 19/00 706/12 |

OTHER PUBLICATIONS

Centers for Disease Control and Prevention. Benefits of Health Promotion Programs. (2013) Available at: http://www.cdc.gov/workplacehealthpromotion/initiatives/workathealth/benefits.html.

Milliman Advanced Risk Adjusters. Available at least as early as Nov. 14, 2016 at: http://us.milliman.com/Solutions/Products/Milliman-Advanced-Risk-Adjusters/.

Johns Hopkins University. About the ACG System. (2013) Available at: https://acg.jhsph.org/index.php/the-acg-system-advantage.

* cited by examiner

| RISK GROUP | PERCENTILE | YEARLY COST | AVERAGE YEARLY COST |
|---|---|---|---|
| 1 | 0-30% | <=$440 | $104 |
| 2 | 30-60% | $440 - $2,373 | $1,167 |
| 3 | 60-80% | $2,373 – 7,643 | $4,428 |
| 4 | 80-100% | > $7,643 | $37,437 |

*FIG. 6A.*

MACHINE LEARNING CLINICAL DECISION SUPPORT SYSTEM FOR RISK CATEGORIZATION

CROSS-REFERENCE TO RELATED APPLICATIONS

This application claims benefit of U.S. Provisional Application No. 62/254,953, titled "Risk Classification for Clinical Decision Support," filed Nov. 13, 2015, which is expressly incorporated by reference in its entirety.

BACKGROUND

With medical care expenses compounding every year, effective population health risk management is essential. Risk stratification systems, for computer assisted clinical decision support, are necessary for determining risks of patient populations in regard to certain conditions and facilitating health management. But present systems for managing population health risks do not harness valuable electronic health record data and claims experience for categorizing patient risks. As a consequence, inaccurate and imprecise risk assignment often results, rendering these systems less effective at understanding their population of patients. This contributes to decreased quality of care, increased risk of medical errors, and increased cost of healthcare. Additionally, specific knowledge of patient risk strata can enable health care administrators to develop wellness programs with population-specific conditions in mind, more accurately forecast future spend levels, and anticipate resource needs. It is of great significance, then, to improve upon conventional technological approaches to achieve a greater degree of accuracy and dependability, especially as applied to a target individual as opposed to a population as a whole—a drawback that conventional approaches have not been able to effectively overcome.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for providing improved risk categorization for clinical decision support. In particular, a risk index is provided that improves on other risk stratification models by synthesizing electronic medical records and health questionnaires with an individual patient's claim histories. One or more machine learning algorithms catalogue patients into distinct group clusters, based on risk which may be associated with annual health care spending, thereby enabling administrators to forecast future spending on the individual and population level. Further, by synthesizing member claims with electronic health records, a more holistic view is provided of patient health. With an improved understanding of the patient population, administrators can more efficiently target individual patients for intervention and develop wellness programs targeting population-specific conditions.

In some embodiments, one or more risk index models are provided that may use information from claims, clinical data, electronic medical records (EMR), and wellness information, which may include personal health assessments (PHA) to classify individuals into risk groups thereby enabling future spending levels to be predicted. Machine learning algorithms may be used in conjunction with historic patient data to determine the risk model(s). In some embodiments, the population risk categories may be displayed to an administrator or clinician to facilitate decision making. Similarly, in some embodiments, a patient may be indexed (or categorized) according to a determined risk index.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee. The present invention is described in detail below with reference to the attached drawing figures, wherein:

FIGS. 6A and 6B depict results from an example embodiment of the disclosure reduced to practice, indicating the determined risk groups and corresponding predicted future costs;

DETAILED DESCRIPTION

Figure 1A:
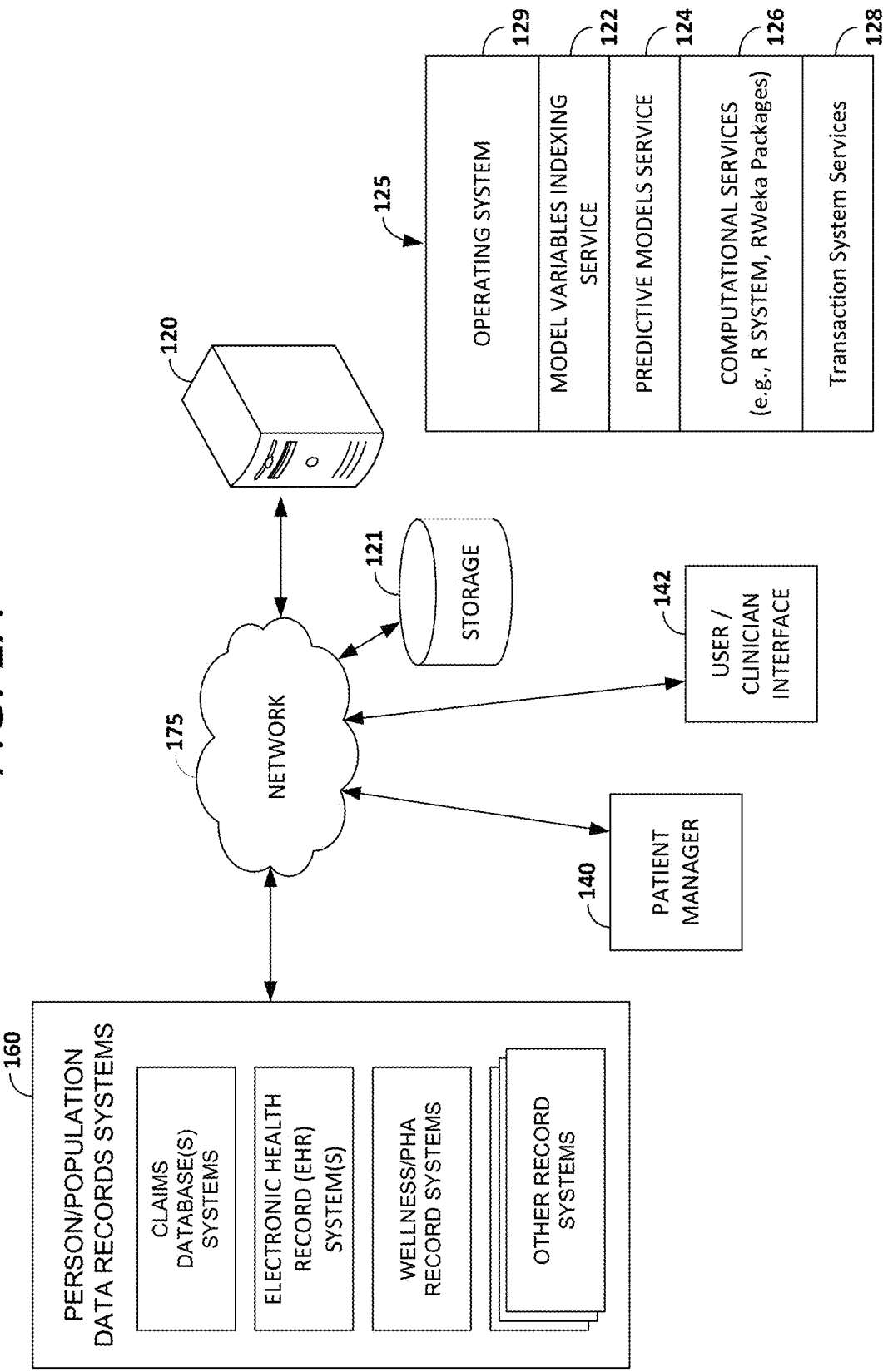
FIGS. 1A, 1B and 1C depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. In one embodiment, computer storage media excludes signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, aspects of the technology described herein are directed towards systems, methods, and computer storage media for, among other things, providing improved risk categorization for clinical decision support. In particular, embodiments may determine a risk index that improves on other risk stratification models by synthesizing electronic medical records and health questionnaires with an individual patient's claim histories. As described previously, in an embodiment, one or more machine learning algorithms classify patients into distinct group clusters, based on risk which may be associated with annual health care spending, thereby enabling administrators to forecast future spending on the individual and population level. Further, by synthesizing member claims with electronic health records, a more holistic view is provided of patient health.

Accordingly, at a high level and in some embodiments, one or more risk index models are provided that may use information from claims, clinical data, electronic medical records (EMR), and wellness information, which may include personal health assessments (PHA) to classify individuals into risk groups thereby enabling future spending levels to be predicted. In some embodiments other data sources may be considered as well; for example, demographic information; other types of claims data, such as pharmacy claims; information about patient lifestyle; diet, living conditions; which may include location; financial condition (e.g. whether the patient is in debt); or other information related to the individual. Data aggregation may be performed on the received raw data and, in some cases interpretive data is determined from the aggregated data. Interpretive data, may include data determined by analyzing the raw data to determining additional data; for example, statistical measurements determined from the raw data.

Using the aggregated and interpretive data (sometimes referred to herein as "composite data"), one or more machine learning algorithms may be applied to determine risk model(s) for classifying patients into risk groups. In particular, machine learning algorithms may be used in conjunction with historic patient data from (the composite data) to determine a set of one or more risk model(s). For example, in one embodiment, an ensemble of Alternating Decision Trees is used, where each decision tree is trained on a random subset of instances and features from the composite patient data. In an embodiment, the specific model(s) are determined based on the types of available patient data, the particular population of patients, the resolution or granularity of risk groups desired, or similar bases. Further, in some embodiments, cost sensitive classification may be used to skew the machine learning algorithm(s) towards over prediction.

The risk index model(s) may be applied to a population of patients to determine a set of resulting risk groups, which may be used for predicting future health spend for both a population and individual basis, as well a level or degree of risk (i.e. how risky) for each risk group or individual group members. In some embodiments, the population risk categories may be displayed to an administrator or clinician to facilitate decision making. Similarly, in some embodiments, a patient may be indexed (or categorized) according to a determined risk index.

In this way, embodiments of the present disclosure can provide an improved understanding of the patient population, thereby enabling administrators to more efficiently target individual patients for intervention and develop wellness programs targeting population-specific conditions. Additionally, embodiments of the present disclosure can positively impact health organizations' key imperatives in a variety of ways such as reduced cost, improved planning, enhanced workplace productivity and morale, reduced worker compensation, disability, and absenteeism costs, improved employee self-image, self-esteem, and well-being.

Figure 2:
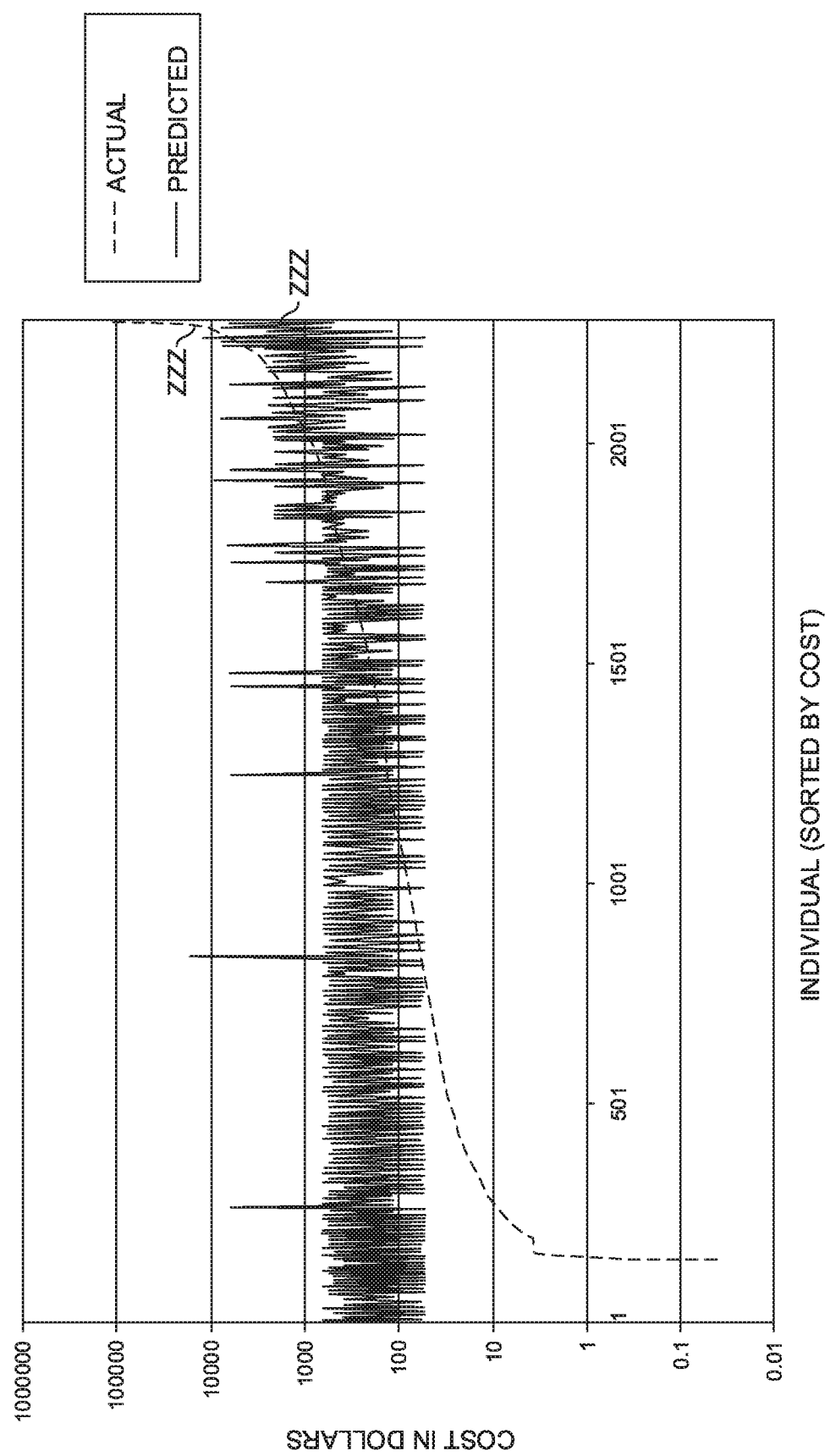
FIG. 2 depicts results from currently utilized methods for forecasting health care spend compared to the actual costs.

As described previously, present approaches for managing population health risks and forecasting health care spend are based largely on medical claims data and do not harness other information, such as valuable electronic health record data, wellness/PHA information, or other claims experience for categorizing patient risks. As a consequence, inaccurate and imprecise risk assignment often results, rendering these systems less effective at understanding their population of patients. Moreover, current approaches largely focus on populations of patients and are not capable of providing reliable information regarding individual patients. For example, a common approach, such as illustratively shown in FIG. 2, is based on actuarial models. With reference to FIG. 2, results of predicted health care spend (202) from such currently utilized methods are shown for a population and compared to the actual costs (204). This particular example approach uses medical claims data (specifically, data regarding costs) for a population of patients. The comparison of the prediction (202) and actual costs (204) shows that this approach is off considerably on both ends for patients who cost a little or a lot. For example, on the high end, where the prediction shows only $10,000, the actual cost is $100,000. Spend forecasts such as shown in FIG. 2 can predict aggregate health care spend in some cases reasonably well, for example, the average (e.g., as shown in the middle portion of the graph of FIG. 2), but do very poorly on an individual level and have not achieved the accuracy of the techniques disclosed herein. In particular, there is far too much variation, person-to-person for such approaches to be useful. Other approaches such as the Milliman Advanced Risk Adjusters (MARA) model, Johns Hopkins Adjusted Clinical Groups (ACG), Truven Health analytics MarketScan are also driven entirely by claims experience, since they are focused on spend (and not risk) and developed by clinicians and actuaries. Their forecasts are based on existing premiums rates. These approaches generally predict spend first and foremost, and specifically, they predict aggregate spend at the population level.

But in contrast to all of these approaches, embodiments of the disclosure taker a different approach to the problem, include other patient data (such as EMRs or Wellness/PHA records, for example), and are thus able to provide more accurate model(s) that also can be used to predict health care spend (or likelihood or risk, or other information) on both the population level and the individual level. Embodiments are capable of achieving significant results over the prior approaches by providing unique techniques that are unknown in the industry and the area of decision support systems. For example, as further described herein, one embodiment synthesizes claim history with clinical and other information from EMRs and/or Wellness/PHA records, and creates forecasts independent of insurance premium rates. More specifically, instead of first predicting spend; one embodiment of the present disclosure first classifies members of the population into risk groups, based on the patient and population data. Then based on the determined risk groups, using information from group members, the embodiment can predict spend level for individual members as well as a degree or level of risk the group members are likely to engage in. This information can then be used to determine spend and risk predictions for the population or for specific groups. Thus, by employing the techniques described herein, embodiments can overcome the deficiencies that are associated with conventional industry practice.

Having briefly described embodiments of the present invention, an exemplary operating environment suitable for use in implementing embodiments of the present invention is described below.

Referring now to the drawings in general, and initially to FIG. 1A in particular, an aspect of an operating environment 100 is provided suitable for practicing an embodiment of the present disclosure. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, example operating environment 100 provides an aspect of a computerized system for compiling and/or running embodiments of monitoring patients and quantitatively predicting for a patient whether or not a condition prevails in the patient, based on a multivariable model involving a plurality of measurements. Environment 100 includes person or population data records systems 160, which may include one or more electronic health record (EHR) systems, claims database(s) systems, wellness/PHA record systems, or other record systems of person (e.g., a patient) or population data (for example information derived from a personal activity such as social network activity, purchase history/spending habits, hobbies, diet, exercise, or other activities regarding a person, which may be determined via questionnaires, or mining social network activity, email, calendar data about a person (which may require consent by the person), financial conditions, other demographic and socio-economic data for a person or population, employment information, social network contacts, or nearly any other such source of information about a person or population. Data records systems 160 may be communicatively coupled to network 175, which is communicatively coupled to computer system 120. In some embodiments, components of environment 100 that are shown as distinct components may be embodied as part of or within other components of environment 100. For example, data records systems 160 (or its subcomponents) may comprise one or a plurality of records systems such as hospital EHR systems, health information exchange EHR systems, ambulatory clinic EHR systems, or other systems having health-related records for one or more patients, and may be implemented in computer system 120. Similarly, data records system 160 may perform functions for two or more of the data records systems (not shown).

Network 175 may comprise the Internet, and/or one or more public networks, private networks, other communications networks such as a cellular network, or similar network (s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of data records systems 160 include one or more data stores of health-related or patient/population records, which may be stored on storage 121, and may further include one or more computers or servers that facilitate the storing and retrieval of the records. In some embodiments, data records system 160 may be implemented as a cloud-based platform or may be distributed across multiple physical locations. Data records system 160 may further include record systems, which store real-time or near real-time patient (or user) information, such as wearable, bedside, or in-home patient monitors, for example.

Example operating environment 100 further includes provider user/clinician interface 142 communicatively coupled through network 175 to an data records system 160. Although environment 100 depicts an indirect communicative coupling between interface 142 and data records system 160 through network 175, it is contemplated that an embodiment of interface 142 is communicatively coupled to data records system 160 directly. An embodiment of interface 142 takes the form of a user interface operated by a software application or set of applications on a server or client computing device such as a personal computer, laptop, smartphone, or tablet computing device. In an embodiment, the application includes the PowerChart® software manufactured by Cerner Corporation. In an embodiment, the application is a Web-based application or applet or a distributed application. A provider clinician application facilitates accessing and receiving information such as from a user or health care provider or insurance company about a specific patient or population of patients including patient history; health care resource data; variables measurements, time series, and predictions (including plotting or displaying the determined results, risk groups, spend forecasts, etc.) described herein; or other health-related information, and facilitates the display of results, recommendations, predictions, orders, or the like, for example. In an embodiment, interface 142 also facilitates receiving orders or recommendations for the patient from the clinician/user, based on the results of risk or spend predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, manager 140 includes a Web-based application or set of applications usable to manage user services provided by an embodiment of the disclosure. For example, in an embodiment, manager 140 facilitates processing, interpreting, accessing, storing, retrieving, and communicating information from data records systems 160 and/or determined risk and spend forecasts for the patient or group(s)/population(s) for which the patient is a member.

Some embodiments of example operating environment 100 includes one or more patient monitors (not shown). A patient monitor comprises one or more sensor components operable to acquire clinical or physiological information about a patient, such as various types of physiological measurements, physiological variables, or similar clinical information associated with a particular physiological status of a patient, and which may be acquired periodically or as one or more time series.

In an embodiment, one or more sensor components of patient monitor(s) may comprise a bedside monitor or a user-wearable sensor component or sensor component integrated into the patient's environment, such as the home or hospital. Examples of sensor components include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables, used according to the embodiment of the invention disclosed herein may be received from human measurements or automatically determined by sensors in proximity to the patient. For example, in one embodiment, a nurse periodically measures a patients' blood pressure and enters the measurement via patient manager 140 or user/clinician interface 142.

In some embodiments, physiological variables may be provided periodically (e.g., hourly, daily, weekly, yearly), continuously, occasionally, such as needed, or even once. Examples of physiological variables monitored or provided by patient monitor(s) can include, by way of example and not limitation, heart rate, blood pressure (e.g., systolic and/or diastolic), oxygen saturation (SoO2), cholesterol (e.g., HDL, LDL, total cholesterol), triglycerides, body mass index (BMI), weight, central venous pressure, other vital signs or any type of measureable or determinable physiological or clinical variable associated with a patient, which may be used for forecasting a future value (of the measured variable, a composite variable based on one or more measured variables, or other factor determined at least in part from one or more measured variables) of a patient in order to facilitate clinical decision making.

In an embodiment, a patient monitor comprises a sensor probe or instrument and a communication link that periodically transmits identification information and probe data to patient manager 140, such that a time series of monitored values is stored on patient manager 140. In an embodiment, patient monitor 140 collects sensor information and performs signal processing, such as movement detection, kinematic modeling, distance and shape processing, velocity measurement, forming a physiological variable decision statistic, cumulative summing, trending, wavelet processing, thresholding, computational processing of decision statistics, logical processing of decision statistics, pre-processing or signal condition, etc., part or all of which may be performed on a patient monitor, patient manager 140, interface 142, and/or computer system 120.

An embodiment of a patient monitor stores user-derived data locally or communicates data over network 175 to be stored remotely. In an embodiment, patient manager 140 is wirelessly communicatively coupled to the one or more patient monitors. Patient manager 140 may also be embodied as a software application or app operating on a user's mobile device. In an embodiment, patient manager 140 and patient monitor(s) are functional components of the same device, such as a device comprising a sensor and a user interface. In an embodiment, manager 140 is embodied as a base station, which may also include functionality for charging the patient monitor(s) or downloading information from monitor(s).

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on patient monitor(s), or patient manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone. This system 120 provides an environment to employ the specific techniques and the specific steps described herein, which is the true focus of this disclosure.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interface 142 and manager 140. In some embodiments, interface 142 operates in conjunction with software stack 125.

In embodiments, model variables indexing service 122 may include services for variables (e.g. the physiological variables or any variable of patient or population information) indexing (or mapping), or services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke one or more computational services 126. In one embodiment software stack 125 includes predictive models service 124, which comprises the services or routines for forecasting a degree of risk for a patient, population, or sub-population (i.e., a risk group), predicting likely future spend levels, forecasting future values of variable(s), for example. Some embodiments of predictive models service include one or more risk index models described herein, and may use computational services 126 to determine and classify population members into risk groups.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, machine learning packages such as RWeka package or similar services for decision trees or other machine learning/classification routines (e.g., random forest, logistic regression). Some embodiments of services 126 comprise a transformation component or service for transforming the physiological or clinical patient information into forecasted value, and a combination component or service for combining successive forecasts into single value. Some embodiments of computation services 126 may use transaction systems services 128. Additionally, some embodiments of computation services 126 may use one or more services stream processing service(s) (not shown).

The stream processing service(s) may be embodied using IBM InfoSphere stream processing platform, Twitter Storm stream processing, or similar complex event processing (CEP) platforms, frameworks, or services, which may include the user of multiple such stream processing services (in parallel, serially, or operating independently). In some embodiments service(s) include the Apache Hadoop and Hbase framework, or similar frameworks operable for providing a distributed file system, and which in some embodiments facilitate or provide access to cloud-based services such as those provided by Cerner HealtheIntent®. In one embodiment, stream processing services listens to at least one "channel" of patient information, which may be provided by patient monitor 141, as patient data or processed information becomes available. Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y"), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with data records systems 160. Further, although depicted as a single storage data store, data store 121 may comprise one or more data stores, or may be in the cloud.

Figure 1B:
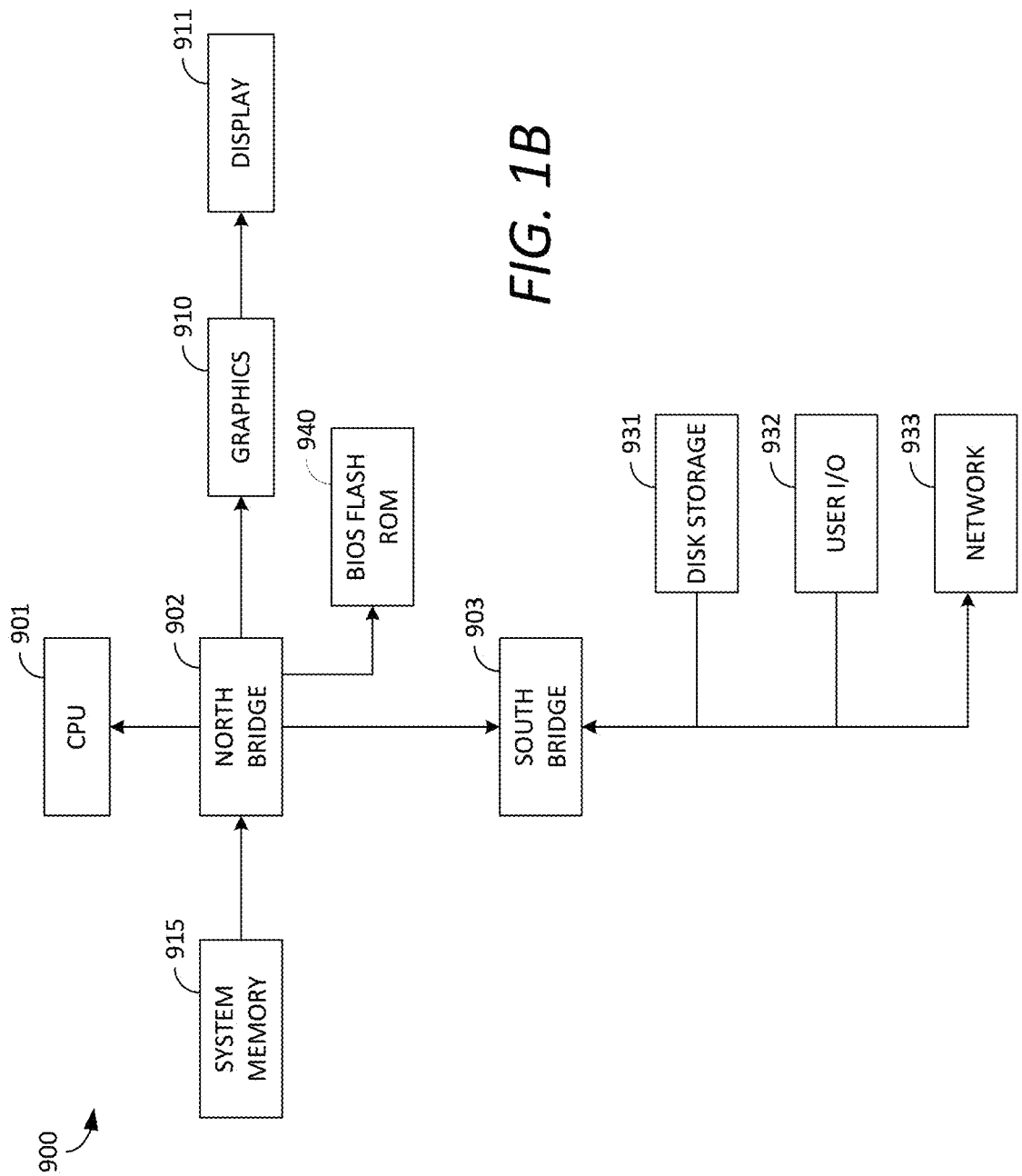

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Embodiments of the disclosure may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like. While embodiments are employed using these types of computing systems, the techniques and processes performed by the computing system are a focus of this disclosure, since it is these techniques and processes that realize the improvement over the drawbacks of the conventional industry practice.

Further, embodiments of the disclosure may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

Figure 1C:
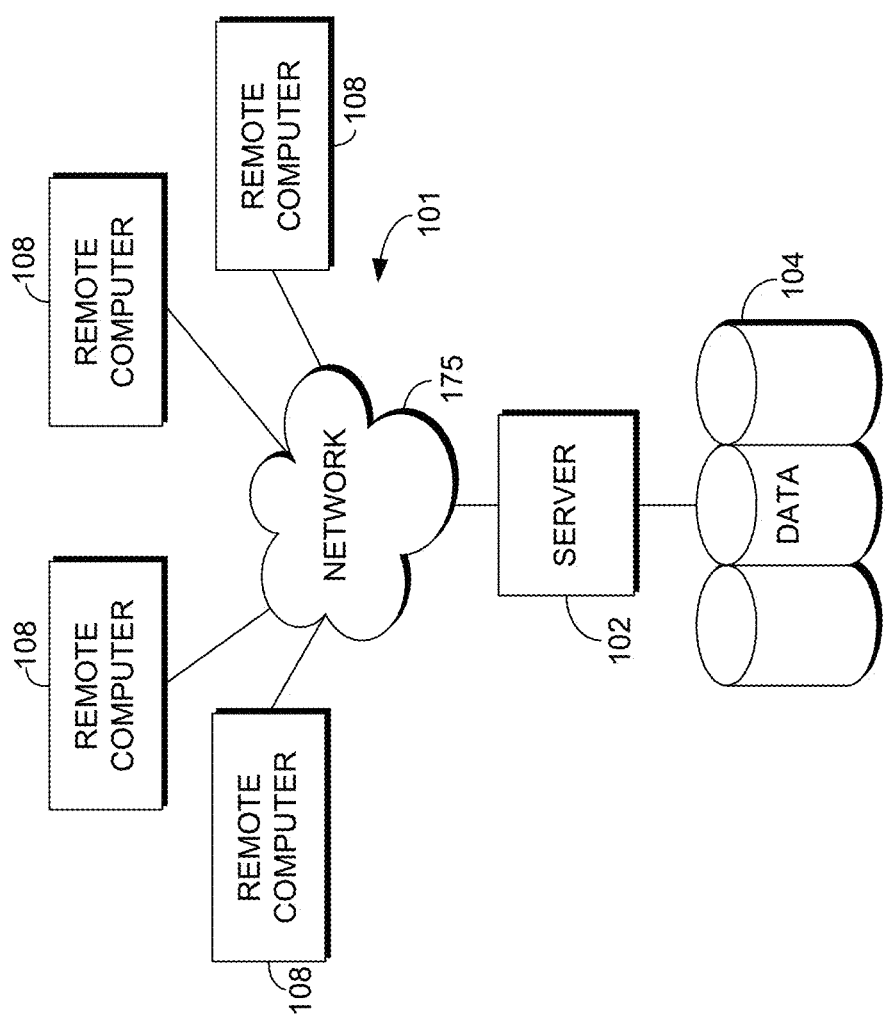

With reference to FIG. 1C, exemplary medical information computing system environment 101 is shown and includes a general purpose computing device in the form of a server 102. In an embodiment, server 102 comprises computer system 120 of FIG. 1A. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media, such as described herein.

The computer storage media discussed above and illustrated in FIGS. 1A and 1C, including storage 121 and database cluster 104, provide storage of computer readable instructions, data structures, program modules, and other data for the server 102. In embodiments, database cluster 104 takes the form of storage 121. In embodiments, database cluster 104 takes the form of a cloud-based data store. In embodiments, the cloud-based data store is accessible by a cloud-based computing platform.

The server 102 may operate in a computer network 175 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices. In embodiments, remote computers 108 comprise computing-devices that are part of a cloud-computing platform and may be embodied as computer system 120. In embodiments, a remote computer 108 is associated with a health records, data source such as data records systems 160, an electronic health record (EHR) system of a hospital or medical organization, a health information exchange EHR, insurance provider EHR, ambulatory clinic EHR, or patient-sensor, or other data source, and facilitates accessing data of the source and communicating the data to server 102 and/or other computing devices on a cloud computing platform, including other remote computers 108.

Computer networks 175 of FIG. 1C may be embodied as network 175 of FIG. 1A. When network 175 is utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnections are well known. Accordingly, additional details concerning the internal construction of the server 102 and the remote computers 108 are not further disclosed herein.

Figure 3:
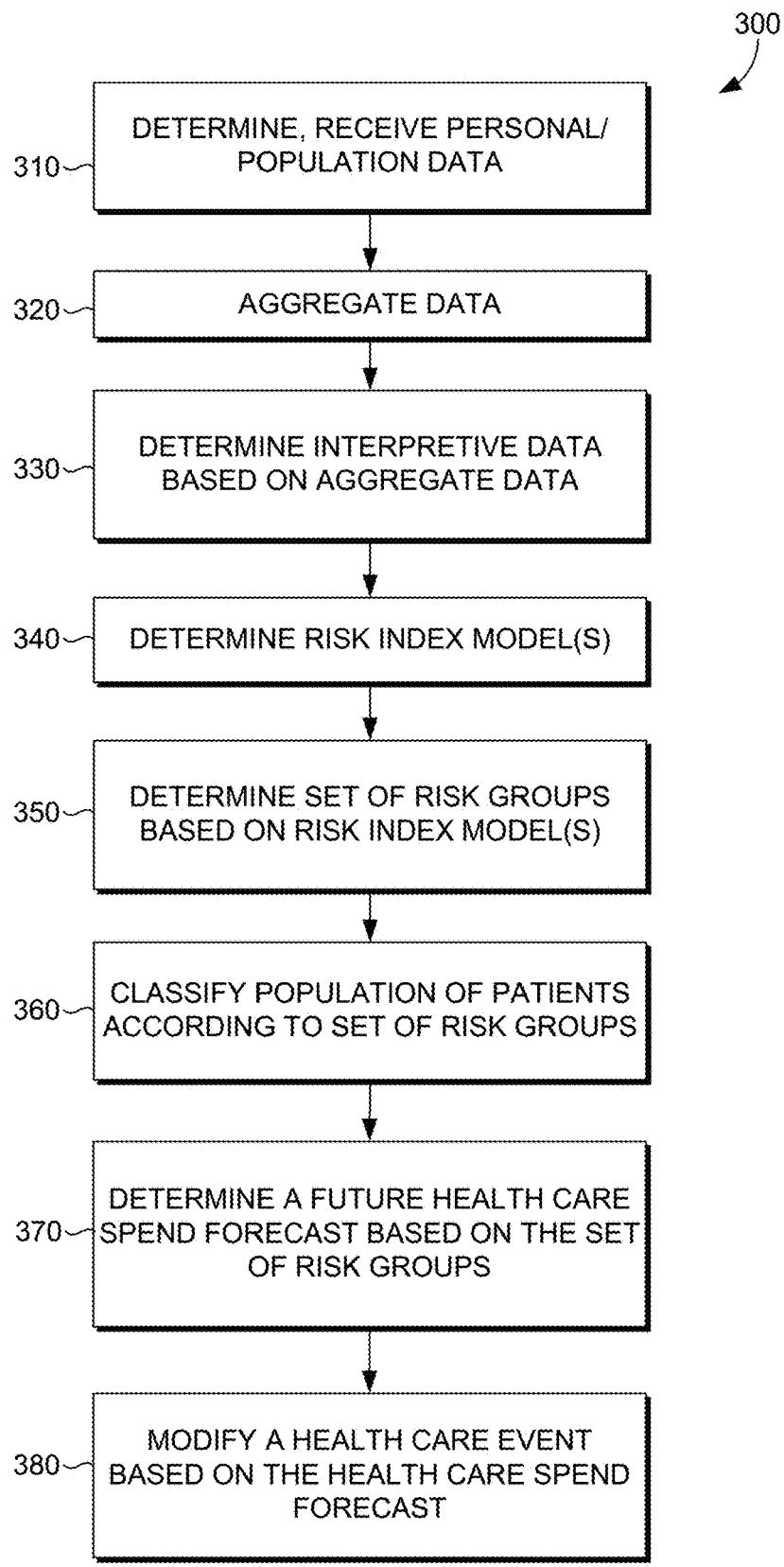
FIG. 3 is a flow diagram of a method for determining a risk index and categorizing members of a population into risk groups, in accordance with embodiments of the invention.

Turning now to FIG. 3, a flow diagram is provided illustrating a method 300 for determining a risk index and categorizing members of a population of humans into risk groups. At a high level, some embodiments of method 300 use historical patient data, such as claims, clinical data, EMRs, and/or wellness information, which may include personal health assessments (PHAs) to classify individuals into risk groups, according to one or more risk models, and thereby predict future spending levels. Initially, as shown at step 310, personal and/or population data is determined and received. Embodiments of step 310 identify a set of data sources and data for one or more human persons in a population of humans and receive the data. Examples of the data include data described in connection to data records systems 160 of FIG. 1A, such as claims data, EMR data, wellness/PHA data, or other types of data related to the persons or population. Thus the determined and received data may correspond to a population of one or more humans. In one embodiment, the data received in step 310 comprises claims data and wellness/PHA information, claims data and EMR data, or claims data, wellness/PHA information and EMR data.

In some embodiments, step 310 further comprises determining a particular population of patients. For example, in one embodiment, a population of patients having a common characteristic, experience, or other similarity may be determined, and data received from this population. In one embodiment, the population comprises a set of patients in a health care system, hospital(s), insurance program, geographical region, health care program, etc. The data may be received form one or more data records systems such as data records systems 160 or other data store or source. In some embodiments, the data is received at a computer system, such as computer system 120 and/or server 102.

At step 320, the data received in step 310 is aggregated. In one embodiment, step 320 comprises collecting the data received in step 310 into a centralized data set, which may be logically centralized (but not actually physically co-located). By aggregating the data in step 320, then at step 330, interpretative data may be determined. Embodiments of step 330 comprise analyzing the "raw" data received in step 310 to determine additional data that may be used for classifying members of the population according to risk groups. In particular, additional data variables may be determined to glean as much information as possible from the claims, clinical encounters, or other data. For example, additional data determined in step 330 may include processed data or data determined (e.g. patterns, clusters, or statistics), inferred, or imputed based on the aggregated data. In some embodiments, the data received at step 310 (sometimes referred to herein as raw data, although such data may represent processed or interpretive data as well) and the interpretive data are combined to form composite data, which may be used in subsequent steps of method 300. Accordingly the term composite data, as used herein may include raw data received in step 310 and/or interpretive data determined in step 330. Components of the composite data may be referred to as features, with specific variables or instances associated with features.

In some embodiments, the composite data includes date regarding: demographic features, clinical features, medical features, pharmacy features, personal health assessment features, behavior or lifestyle features, and/or aggregate spending levels. By way of example and not limitation, demographic features may include data relating to age, gender, race, socio-economic variables, which may also include financial conditions and living conditions, environment, and/or region. Clinical features may include Systolic blood pressure, Diastolic blood pressure, HDL cholesterol, LDL cholesterol, Triglycerides, Total cholesterol, Body mass index (BMI), or other physiological variables. In some embodiments, median values may be sued where multiple encounters are recorded over the course of a year.

Medical features may total spending for each of the top X-number of medical conditions (indicated by the ICD-9 codes from the aggregated population) incurred by the member (for example the top 30 medical conditions); total count of each of these top X-number of medical conditions (indicated by the ICD-9 codes from the aggregated population) incurred by the member; Top three (or top Y-number of) costliest ICD-9 claim codes, based on annual spending (where Y is less than 10 in some embodiments), for conditions where total annual spending is: greater than $500 per year; between $250 and $500 per year; or between $100 and $250 per year, for example. (Other ranges may be used as appropriate); summary statistics detailing the minimum, mean, median, and maximum claim amount per individual; and/or summary statistics detailing the minimum, mean, median, maximum, and total claim encounters per individual. It is contemplated that in some embodiments, X-number and Y-number described above can vary from these above examples, based on the desired number medical features.

Pharmacy features may include total spending for each of the top M-number of pharmacy classes (indicated by the therapeutic class codes from the aggregated population) incurred by the member (for example, M is 30 in one embodiment); total count of each of the top M-number of pharmacy classes (indicated by the therapeutic class codes from the aggregated population) incurred by the member; top three (or N-number of) costliest therapeutic class codes, based on annual spending (where N is less than 10 in some embodiments), for prescriptions where the total annual spending per class is: greater than $500 per year; between $250 and $500 per year; or between $100 and $250 per year, for example. (again, other ranges may be used as appropriate); summary statistics detailing the minimum, average, median, and maximum prescription cost per individual; and/or summary statistics detailing the minimum, average, median, maximum, and total prescriptions filled per individual.

Personal health assessment features may include information (which may be derived ultimately from questionnaires or PHAs) regarding indications specifying whether the individual has certain conditions such as anxiety, sleep apnea, asthma, frequent headaches, high blood pressure, diabetes, severe allergies, and so forth; indicators specifying whether the individual had previously been diagnosed with cancer(s); indicators specifying when the individual last had health screenings such as mammograms, prostate/pap exams, etc.; indications as to whether the member is pregnant or plans on getting pregnant in the next year; or any other information derived from or related to PHAs used for determining risk group(s).

Behavior or lifestyle features may include information derived from social networks, purchase history/spending habits, hobbies, diet, exercise, or other activities regarding a person, gym membership, vacation(s) or recreational activities, financial information (such as debt, income level), employment information, job satisfaction, community/ friends, religion/spirituality, social network contacts, other personal activity information, or nearly any other such source of information relating to behavior or lifestyle.

Aggregate spending levels may include annual medical spending, annual pharmacy spending, and/or annual total spending (e.g., medical+pharmacy), for example. In one embodiment, the composite data is structured as a data panel.

At step 340, one or more risk index models are determined. Embodiments of step 340 determine one or more risk models to classify members of the population into one or more risk group(s). Risk models may be determined based on the data available (i.e. the composite data determined from steps 310 through 330). In some embodiments, one or more pre-determined risk models are selected at step 340, and in some embodiments the one or more risk models may be generated (or pre-determined risk models may be updated). In particular, in an embodiment of step 340, a simple selection process is used initially to determine the risk model(s), based on the available data. In this embodiment, where at least EMR, PHA, and claims data is available, a claims, EMR, and PHA model is selected (or determined). If at least EMR is not available, then where at PHA data and claims are available, then a claims and PHA model is selected (or determined). Finally, according to this example embodiment, if PHA data and EMR are not available, then a claims-only model is selected (or determined).

In some embodiments of step 340, the one or more risk models are generated (or updated) using machine learning algorithms (such as described in connection to computation services 126 of FIG. 1A). In some embodiments of step 340, a risk model is determined by identifying a sample of data from a particular population over a specified time period, and dividing the sample of data into a training set and a testing set of data. The training set of data may be used to build and/or train the model, and the testing set may be used to evaluate the model (and in some cases further modify, such as by adjusting weights). For example, if the sample of data spans 3 years, the training set may comprise data for years 0-2 and the testing set may comprise data for years 2-3.

One or more machine learning algorithms may be used to develop the risk model(s). According to one embodiment an ensemble of alternating decision trees is used to build the risk model(s). Each decision tree is trained on a random subset of instances and features of the composite data. In some embodiments, the number of decision trees used is based on the data, population, or properties of the risk groups. For example, in one embodiment the number of decision trees is approximately 50. It is worth noting that too many trees may overstrain the data and result in an undesirable outcome. In one embodiment, the ensemble algorithm is majority rule, and in one embodiment it is weighted; for example, new ensemble members may be weighted less or ensemble members may be weighted according to past performance (e.g., the smart student is weighted more). In some embodiments, the R package RWeka classifier is used for implementing the alternating decision trees. In some embodiments, cost-sensitive classification is employed to skew the machine learning algorithm(s) towards over prediction. In particular, it is generally desirable that a risk model over predict spending than under-predict spending. The cost-sensitive classification may be reflected as a weighting, in one embodiment, such as a penalizing factor in the alternating decision trees thereby biasing towards over prediction.

Figures 5A, 5B, 5C:
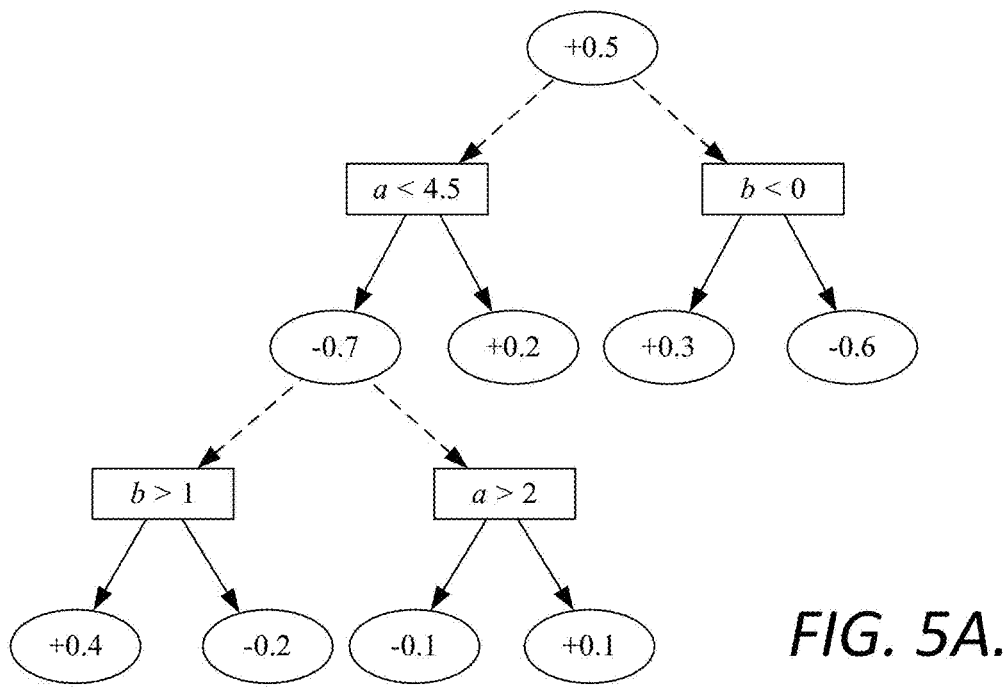
FIGS. 5A-5C illustratively depict aspects of one example risk index algorithm, in accordance with embodiments of the invention.

With reference to FIGS. 5A, 5B, and 5C (and continuing reference to FIG. 3), aspects of an example risk index model based on alternating decision trees are illustratively depicted. A generic decision tree is a decision support tool which arrives at a decision after following steps or rules along a tree-like path. While most decision trees are only concerned about the final destination along the decision path, alternating decision trees take into account every decision made along the path and may assign a score for every decision encountered. Once the decision path ends, the algorithm sum all of the incurred scores to determine a final classification. FIG. 5A depicts an example of a generic alternating decision tree. In this example, the model starts with a score of 0.5, then depending on the response to the first question, will take either the left and right path, ask another question, collect another score, and so forth until a terminal node is reached. Then, all incurred scores will be added together and used to determine the final classification.

In some embodiments, the alternating decision tree algorithm may be further customized. For example, the alternating decision tree algorithm may be modified by wrapping it in other algorithms, such as: a cost-sensitive classifier, a multi-class classifier, and/or a rotation forest ensemble method. With regards to the cost-sensitive classifier algorithm, this classifier may be used to encourage the over-prediction and penalize the under-prediction, of spending in the Risk Index model, such as described previously. Generally, machine learning algorithms do not assign a quantitative meaning to the classes they create. For example, in one embodiment of a Risk Index model, an individual assigned a risk index of 2 is not necessarily twice as costly as someone indicated as a 1. To penalize specific misclassifications, such as under-prediction or over-prediction, models can employ a cost-sensitive classifier and adjust penalty weights.

Without a cost-sensitive classifier, a machine learning algorithm may use a generic cost matrix, such as shown in FIG. 5B. The intuition behind the cost matrix is as follows. If the model predicts a member to be classified in group A, and the member really should be in group A, no penalty is assigned. However, if this same member is predicted to be in group B, C, or D, a 1-point penalty will be assigned to the model for this misclassification, regardless of which group the member was predicted to be in. Thus, all misclassifications are penalized equally. However, by adjusting the cost matrix, penalties for specific misclassifications can be assigned. For example, where someone who was truly in group D was classified in group A, the model could increase the penalty in that section of the cost matrix, such as shown in FIG. 5C. With reference to FIG. 5C, it can be seen (item 501) that it is 5 times as costly for the model to assign someone to category A when they really should belong to category D. A cost matrix such as this may be adjusted as needed to help fine tune the model for different iterations, and may be based on the specific population in some embodiments.

With regards to a multi-class classifier, some machine learning algorithms, such as alternating decision trees, generally only allow for the classification into two categories (e.g. a binary classification). In cases where it is desired to classify three or more categories (such as with some embodiments of the Risk Index model(s), which may segments groups into four or more classes), a multi-class classifier is used.

In order to assist the alternating decision tree in selecting best features for predictive modeling, an ensemble method called rotation forest may be used. The rotation forest algorithm randomly splits the dataset into a specified number of subsets and uses a clustering method called Principal Component Analysis to group features deemed useful. Each tree is then gathered (i.e., "bundled into a forest") and evaluated to determine the features to be used by the base classifier.

Various alternative classifiers may be used for the Risk Index algorithm, however the above wrappers, in conjunction with the alternating decision tree, generally performed best based on models reduced to practice and were therefore selected most often as the algorithm for the Risk Index model. Thus, although the Risk Index model(s) described herein in connection to the embodiments reduced to practice was calibrated using the alternating decision tree algorithm, this does not mean the models must always be based on an alternating decision tree. Indeed, there are thousands of machine learning algorithms, which could be used in place of, or in conjunction with, the alternating decision tree algorithm. For example, one set of alternative classifiers comprise ensemble methods.

Ensemble methods use multiple, and usually random, variations of learning algorithms to strengthen classification performance. Two of the most common ensemble methods are bagging and boosting. Bagging methods, short for "bootstrap aggregating" methods, develop multiple models from random subsets of features from the data ("bootstrapping"), assigns equal weight to each feature, and selects the best-performing attributes for the base classifier using the aggregated results. Boosting, on the other hand, learns from the data by incrementally building a model, thereby attempting to correct misclassifications from previous boosting iterations. The Rotation Forest wrapper used by some embodiments of the Risk Index model is an example of an ensemble method.

Regression models are frequently used to evaluate the relationship between different features in supervised learning, especially when trying to predict a value rather than a classification. However, regression methods are also used with other methods to develop regression trees. Some algorithms combine both classification and regression methods; algorithms that used both methods are often referred to as CART (Classification and Regression Trees) algorithms.

Bayesian statistical methods are used when the probability of some events happening are, in part, conditional to other circumstances occurring. When the exact probability of such events is not known, maximum likelihood methods are used to estimate the probability distributions. A textbook example of Bayesian learning is using weather conditions, and whether a sprinkler system has recently gone off, to determine whether a lawn will be wet. However, whether a homeowner will turn on their sprinkler system is influenced, in part, to the weather. Bayesian learning methods, then, build predictive models based on calculated prior probability distributions.

Another type of classifiers comprise artificial neural networks. While typical machine learning algorithms have a pre-determined starting node and organized decision paths, the structure of artificial neural networks are less structured. These algorithms of interconnected nodes are inspired by the neural paths of the brain. In particular, neural network methods are very effective in solving difficult machine learning tasks. Much of the computation occurs in "hidden" layers.

By way of example and not limitation, other classifiers and methods that may be utilized include (1) decision tree classifiers, such as: C4.5—a decision tree that first selects features by evaluating how relevant each attribute is, then using these attributes in the decision path development; Decision Stump—a decision tree that classifies two categories based on a single feature (think of a single swing of an axe); by itself, the decision stump is not very useful, but becomes more so paired with ensemble methods; LADTree—a multi-class alternating decision tree using a LogitBoost ensemble method; Logistic Model Tree (LMT)—a decision tree with logistic regression functions at the leaves; Naive Bayes Tree (NBTree)—a decision tree with naive Bayes classifiers at the leaves; Random Tree—a decision tree that considers a pre-determined number of randomly chosen attributes at each node of the decision tree; Random Forest—an ensemble of Random Trees; and Reduced-Error Pruning Tree (REPTree)—a fast decision tree learning that builds trees based on information gain, then prunes the tree using reduce-error pruning methods; (2) ensemble methods such as: AdaBoostM1—an adaptive boosting method; Bagging—develops models using bootstrapped random samples, then aggregates the results and votes for the most meaningful features to use in the base classifier; LogitBoost—a boosting method that uses additive logistic regression to develop the ensemble; Multi-BoostAB—an advancement of the AdaBoost method; and Stacking—a method similar to boosting for evaluating several models at the same time; (3) regression methods, such as Logistic Regression—regression method for predicting classification; (4) Bayesian networks, such as BayesNet—Bayesian classification; and NaiveBayes—Bayesian classification with strong independence assumptions; and (4) artificial neural networks such as MultiLayerPerception—a forward-based artificial neural network.

Returning to FIG. 3 and specifically step 340, in some embodiments, the decision trees may be used for feature selection, and in some embodiments, the risk models may further provide information identifying which features (or variables) of data were most significant in the prediction (i.e., which features are more meaningful for prediction of health care spend). Further, in some embodiments, these significant features may be weighted in an implemented model. Although the previous examples describe using alternating decision trees, this is only one example of suitable machine learning algorithm(s) that may be used for determining the risk model(s). Other machine learning algorithms might include random forest, linear logistic models, proportional hazard model, or other similar classification algorithms known to those skilled in the art. The particular model(s) and configuration used may be dependent on the data, the type of data (e.g. claims, wellness/PHA, and/or EHR) the population or criteria for the risk group(s), such as the number of groups, resolution, or other properties.

In some embodiments, the model may be evaluated for accuracy based on an exact match (prediction equals actual) plus over-prediction, such that false negatives are only counted when the model under predicts. In this way, over prediction (i.e., predicting higher spend than what actually occurs) is not considered a miss, because this is considered a savings. The evaluation may be used for updating or modifying the model to be more accurate, for weighting the model, or for replacing the model with a more accurate one.

Figure 6B:
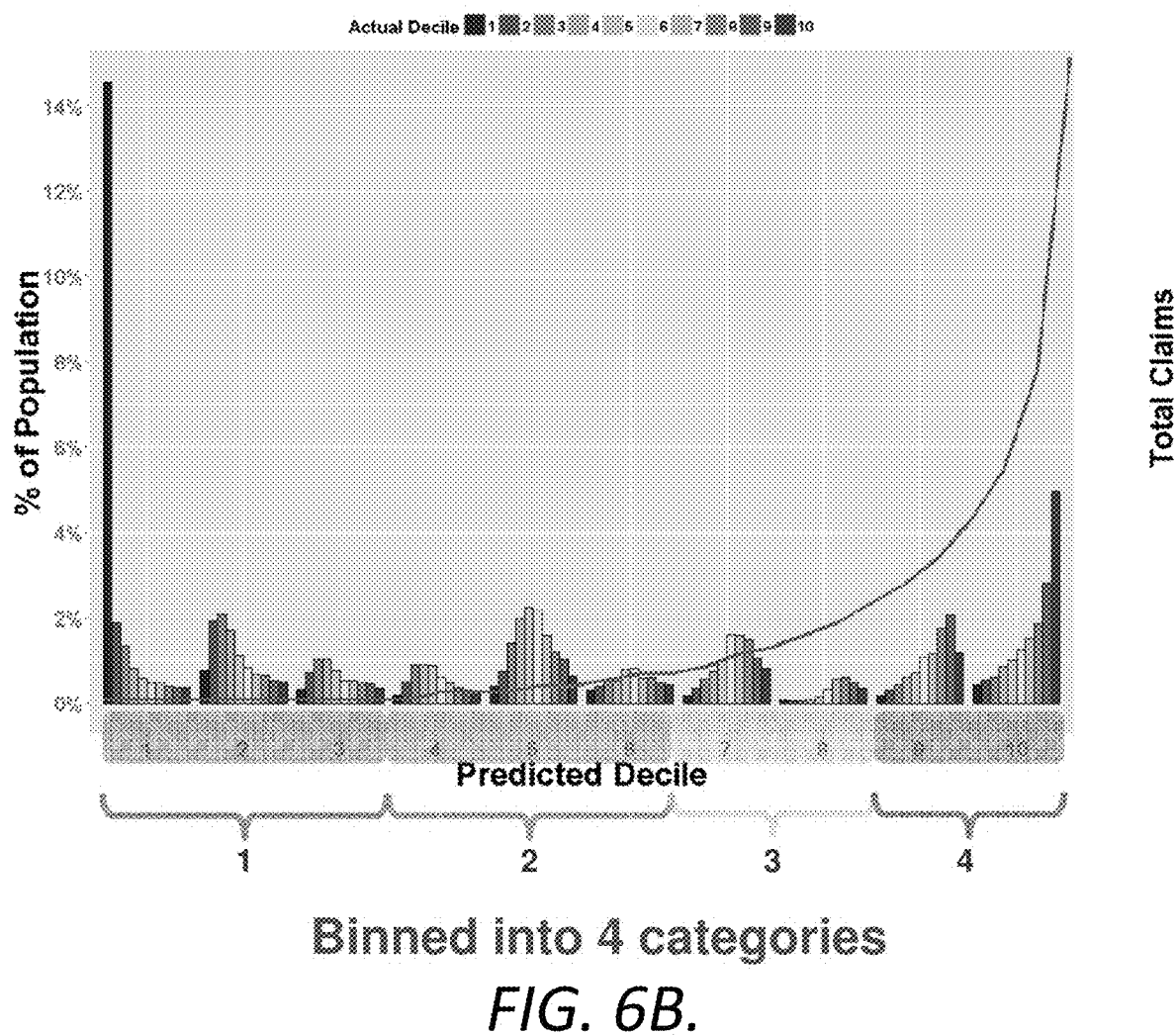

At step 350, a set of risk groups are determined based on the risk index model(s) determined in step 340. Embodiments of step 350 determine the risk groups for classifying the population of patients, based on the risk index model(s) and composite data. At step 360, the population of patients is classified according to the set of risk groups determined in step 350. In some embodiment, steps 350 and 360 are determined at the same time, as an output of the risk index model. For example, the machine learning algorithms determined in step 240 may be applied to the historical population member data (the composite data) to categorize individual member's predicted risk group and associated annual health care spending. In this way, members are classified into the risk groups, as a result of machine learning classification. In one embodiment, which was reduced to practice, four risk groups are determined as shown in FIGS. 6A and 6B.

At step 370, a future health care spend forecast is determined based on the set of risk groups. Embodiments of step 370 may determine a forecast of future health care spend for individual population members, or for one or more of the risk groups, which may be used to predict spend for the population. An example embodiment, which was reduced to practice, showing a spend forecast, such as determined in step 370, is shown in FIG. 6A.

At step 380, a health care event is modified based on the health care spend forecast. Embodiments of step 380 may modify (or determine) a health care event associated with at least one member of a population classified according to method 300. Examples of modifying a health care events may include, without limitation, a health care experience for the at least one member of the population, a care program or care pathway such as a computer program specifying a regimen of treatment, an incentive program, modifying a fee or billing procedure (such as changing a fee or advanced billing, for example), an order, cost, premium, treatment, consultation, billing program, modifying insurance coverage, hedging costs, modifying resource staffing, or any other health care related event, activity, occurrence, transaction, or the like. In an embodiment, an electronic record associated with the individual member (i.e., patient) is altered to indicate that the member is classified according to a particular risk group or is associated with a particular likely future spend level.

Figure 4:
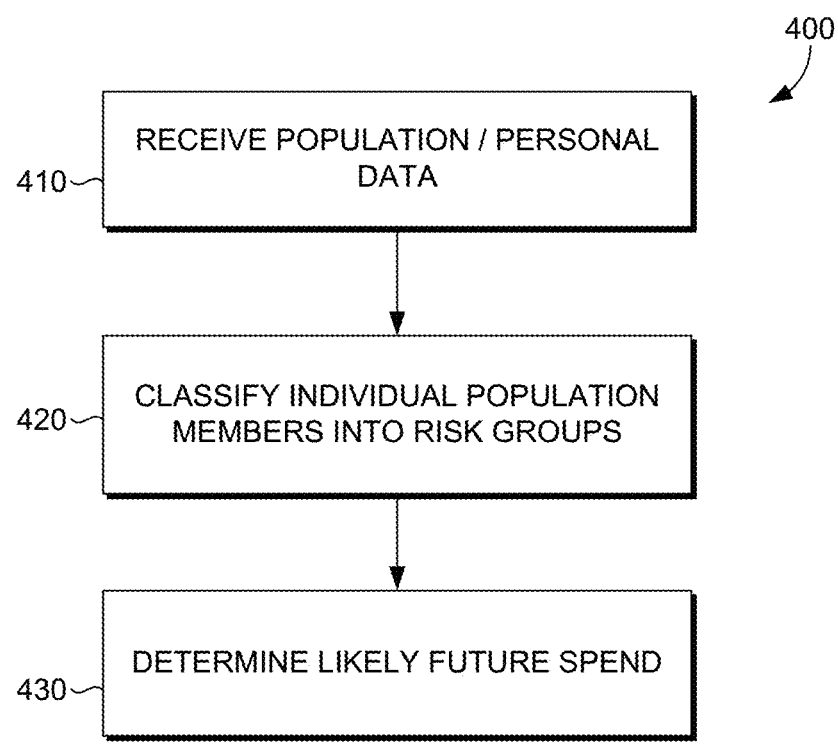
FIG. 4 is a flow diagram of a method for predicting likely future spend for a population of patients and/or for individual members, in accordance with embodiments of the invention.

Turning now to FIG. 4, a flow diagram is provided illustrating a method 400 for predicting likely future spend for a population of patients and/or for individual population members. At a high level, some embodiments of method 400 use historical patient data, such as claims, clinical data, EMRs, and/or wellness information, which may include personal health assessments (PHAs) to classify individuals into risk groups, according to one or more risk models, and thereby predict future spending levels. Initially, at step 410, population or personal (population member) data is received. Embodiments of step 410 may receive data from one or more data records systems, such as data records system 160 described in FIG. 1A. Some embodiments of step 410 may be implemented as described in step 310 of method 300 (FIG. 3), and in some embodiments, the data received in step 410 may be used to determine composite data (or may be composite data) such as described in steps 310-330 of method 300.

At step 420, individual population members are classified into risk groups. Embodiments of step 420 classify individuals into risk groups by applying a risk index model(a) (or one or more machine learning algorithms, which may be part of the risk index model) to the received data of the individuals (received in step 410). Some embodiments of step 420 are implemented as described in step 360 of method 300. In one embodiment, the number of risk groups is based on the population; for example the number of population members. In one embodiment four risk groups are determined, and in another embodiment 10 risk groups are determined.

At step 430, likely future spend is determined for members classified into each of the risk groups. In some embodiments the likely future spend is determine for a specific duration of time, such as for the next year, next 3 years, next 5 years, etc. An example of predicted future spend, for members classified into one of four risk groups, is illustratively shown in FIG. 6A. Some embodiments of step 430 are determined as described in step 370 of method 300. In some embodiments, after classifying members of a population according to risk (step 420), historic spend is analyzed for each risk group and used as a basis for determining future spend for the risk group. Some embodiment of method 400 may further comprise modifying a health care event based on the health care spend forecast such as described in step 380 of method 300.

With reference now to FIGS. 6A-7B, an example embodiment of the disclosure was reduced to practice. The example embodiment used an ensemble of 50 alternating decision trees as machine learning algorithms for a risk index model. In particular, the R-System with the R-package RWeka was used to implement the ensemble of alternating decision trees. Population data was acquired from two populations: Advocate Health Care, which include claims data and EMR data, and Cerner Health Plan, which included claims data, EMR data, and Wellness/PHA data. Population members were classified into 10 groups, initially, which were then binned into four risk groups (see FIG. 6B). Based on these four risk groups, future health care spend was predicted, as shown in FIG. 6A.

Figure 7A:
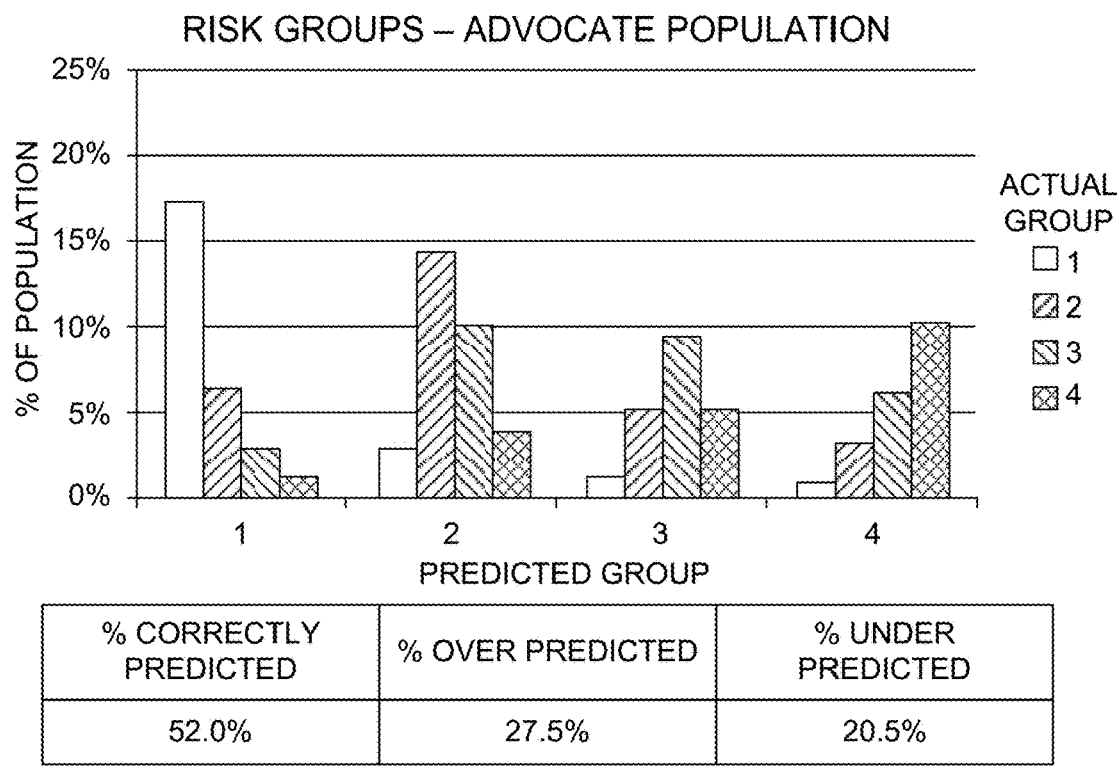
FIGS. 7A and 7B depict results from the example embodiment reduced to practice described in FIGS. 6A-6B as applied to populations of patients from Advocate Health Care and Cerner Health Plan.
Figure 7B:
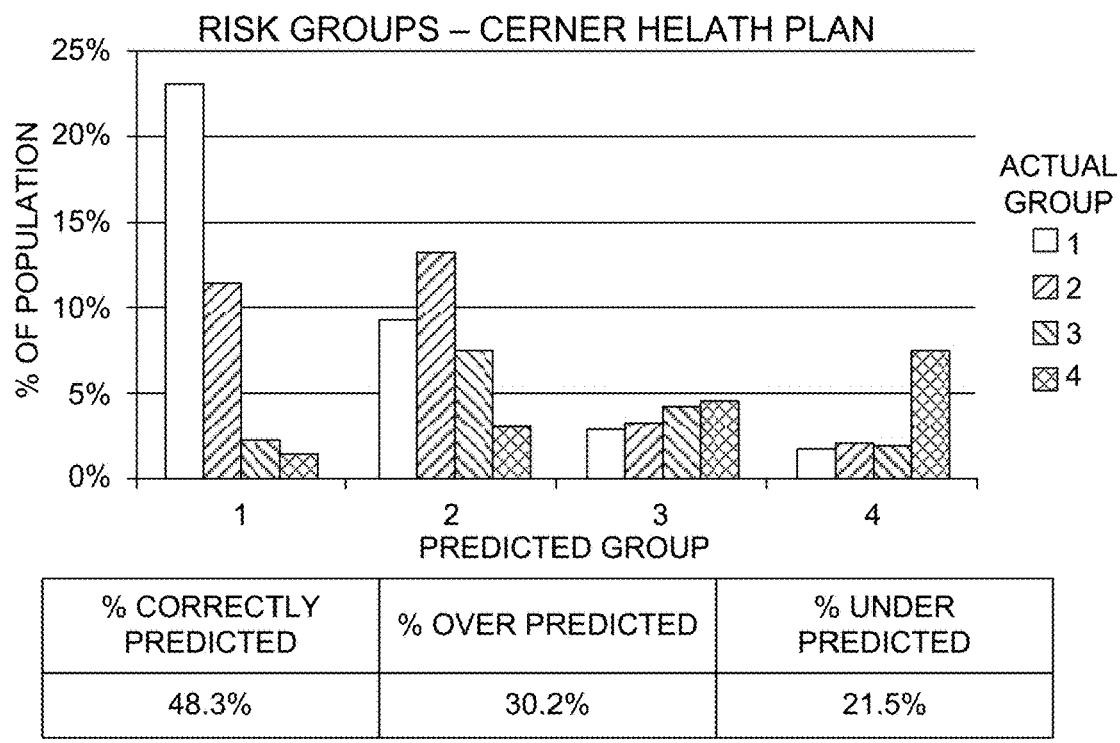

FIGS. 7A and 7B show the results of the embodiments of the risk index model reduced to practice as applied to the two populations of data. In particular, the predicted spend levels for each risk group is shown in comparison to the actual spend. As shown in the table beneath each graph, the model is approximately 80% when combined with over-predicted results. In particular, with regard to FIG. 7A, the total spend predicted (for a particular test year—2013) was $295,032,801; the actual cost was $276,913,725, for a difference of only $18,119,076 or 7%.

Figure 8A:
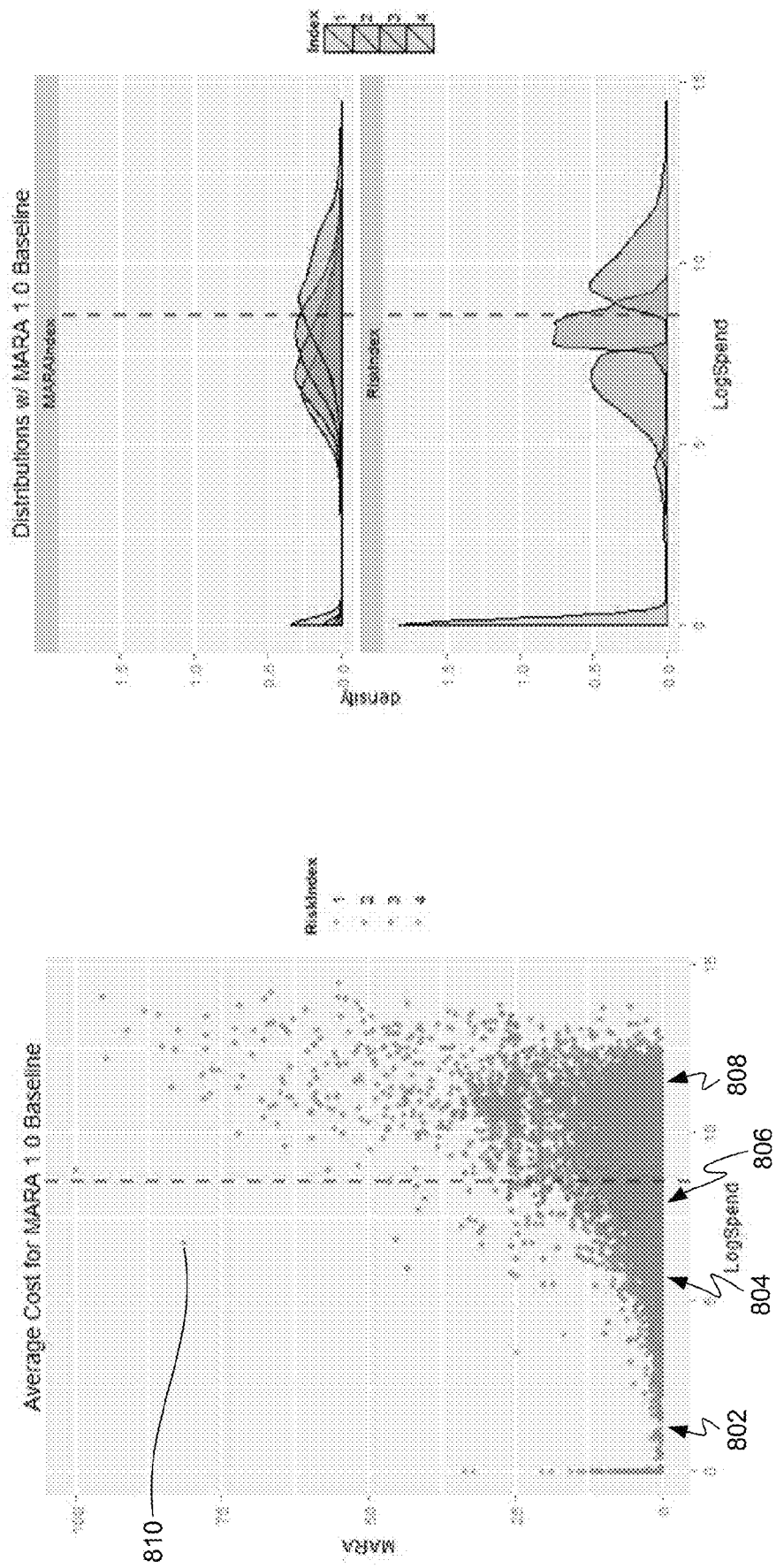
FIGS. 8A and 8B show a comparison of the results from the example embodiment reduced to practice vs. the Milliman Advanced Risk Adjusters (MARA) technique for determine risk.
Figure 8B:
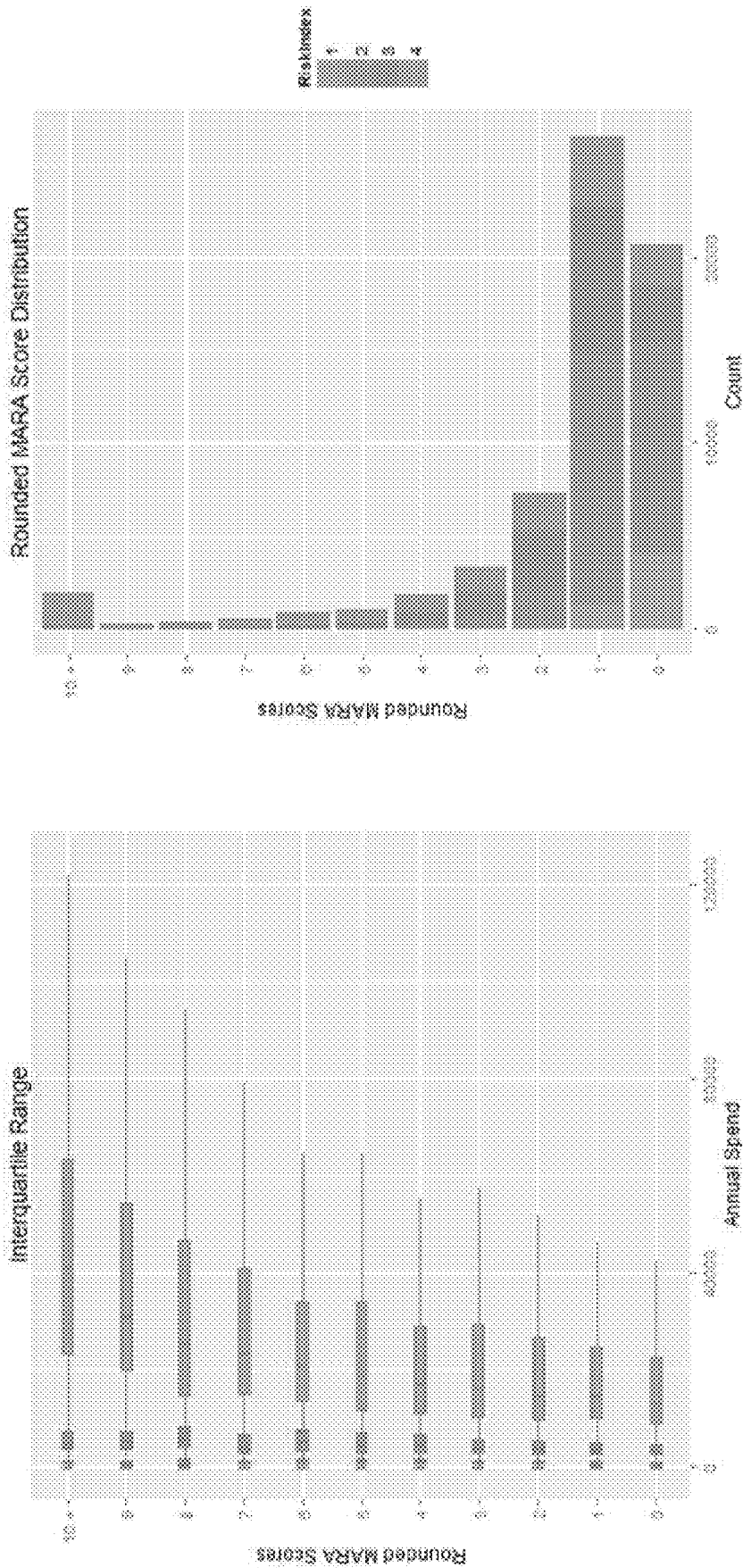

FIGS. 8A and 8B show results of the risk model embodiment compared to the Milliman Advanced Risk Adjusters (MARA) approach for determine risk. FIG. 8A shows an average cost for MARA and FIG. 8B shows log distributions. As can be seen in FIG. 8A, a considerable number of data points show low MARA scores on the y-axis (correlating to a lower risk) but a high spend on the x-axis, such as shown on the lower right cluster of plots 808. Note, the x-axis is displayed as a log scale, where exp(5)=$148 and exp(10)=$22,000. Inaccuracies occur when, for example, conventional approaches deem data points such as 810 as having a high MARA score but, in reality, have a low spend. Similarly, inaccuracies occur when data points are given a low MARA score but end up having a high spend, such as lower right cluster 808. FIG. 8A depicts these drawbacks and inaccuracies of conventional technologies since the conventional method did not accurately predict the population in the lower right cluster 808 as having a high MARA score.

The advantages of the embodiments' technical solution are clearly demonstrated as embodiments gather particularized data from unique data sources and rely on unconventional techniques to overcome the deficiencies found within the prior art. For example, the lower right cluster 808 was accurately classified into group four (correlating to the most expensive and riskiest group), while the conventional approach classified—in error—this lower right cluster 808 as having a lower risk. Similarly, the model embodiment accurately predicted a lower spend for members associated with risk index of 1, shown at 802; a moderately higher spend for members associated with risk index of 2, shown at 804; and an even higher spend for members associated with risk index of 3, shown at 806. As such, applying the techniques described above accomplishes new and improved results, which were impossible to achieve using conventional techniques and technology.

As these figures demonstrate, the application of the current embodiments has a significant advantage over conventional clinical support systems. By employing one of the technical solutions described herein, embodiments have a greater degree of accuracy and reliability that were not yet realized in conventional technological solutions. Further, while the disclosed techniques are certainly accurate when applied to populations, they are also accurate when applied to a target individual. This is in contrast to conventional approaches, which are applied primarily at a population level due to its inefficiencies stemming from limited data sources and conventional analyses.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized system comprising:
    a risk index classifier configured to classify members of a population of humans into one or more risk groups from a set of risk groups;
    one or more processors; and
    computer storage memory having computer-executable instructions stored thereon which, when executed by the processor, implement a method of predicting likely future health care spend for the population members, the method comprising:
    receiving a set of member data for a plurality of members of the population;
    determining one or more risk index models used by the risk index classifier based on a type of the set of member data, the one or more risk index model determined using a set of machine learning algorithms;
    classifying, using the risk index classifier, one or more members of the population into one or more risk groups from the set of risk groups, based on the set of member data;
    determining a future health care spend forecast for the classified one or more members of the population; and
    modifying a health care event based on the determined forecast,
    wherein the set of member data comprises data related to claims and data related to at least one of (i) wellness or personal-health-assessment (PHA) information and (ii) electronic medical record (EMR) information.

2. The computerized system of claim 1, wherein the modified health care event comprises selecting or modifying a computer health care treatment program associated with the classified one or more members of the population.

3. The computerized system of claim 1, wherein the set of member data comprises data related to claims, wellness or personal-health-assessment (PHA) information and electronic medical record (EMR) information.

4. The computerized system of claim 1, wherein determining a future health care spend forecast is based at least in part on the received set of member data.

5. The computerized system of claim 1, wherein one or more index models are determined at least based on the received set of member data.

6. The computerized system of claim 1, wherein the set of machine learning algorithms comprises an ensemble of alternating decision trees.

7. The computerized system of claim 6 wherein the set of machine learning algorithms further comprises a cost-sensitive classifier, a multi-class classifier, and a rotational forest ensemble method.

8. The computerized system of claim 1 wherein the set of machine learning algorithms comprises a cost-sensitive classifier.

9. The computerized system of claim 1 further comprising determining the number of risk groups in the set of risk groups, based in part on the received set of member data.

10. The computerized system of claim 1, wherein the set of member data comprises data related to claims and behavior or lifestyle information.

11. A method for predicting likely future health care spend for individual members of a population of humans using a computing system, the method comprising:
    receiving electronic data over a communications network for the members of the population, the data comprising historical information related to claims and data related to at least one of (i) wellness or personal-health-assessment (PHA) information and (ii) electronic medical record (EMR) information;
    determining, via the computing system, one or more risk index models used by risk index classifier based on a type of the received data, the one or more risk index models determined using a set of machine learning algorithms;
    classifying, via the computing system, members of the population into a set of risk groups, based on the received data and a risk index model, the risk index model using one or more machine learning algorithms; and
    determining, via a computing system, a set of future health care costs over a duration of time associated with the classified members based on the classification and the received data.

12. The method of claim 11 further comprising modifying a health care event based on the determined set of future health care costs.

13. The method of claim 11, wherein the one or more machine learning algorithms comprises an ensemble of alternating decision trees.

14. The method of claim 13, wherein the set of machine learning algorithms further comprises a cost-sensitive classifier.

15. The method of claim 11 further comprising determining a future health care cost the over a duration of time for the population based on the set of future health care costs associated with the classified members.

16. One or more non-transitory computer-storage media having computer-executable instructions embodied thereon that, when executed by a computing device, cause the computing device to perform a method of determining future health care costs for members in a population of human patients, the method comprising:
    receiving raw data for the members in the population, the raw data comprising claims information and at least one of (i) wellness or personal-health-assessment (PHA) information and (ii) electronic medical record (EMR) information for each of the members;

determining a risk index model based on the raw data, a type of the raw data, and a set of machine learning algorithms;

classifying the members of the population into one or more risk groups using the risk index model;

determining a future health care costs over a duration of time for the members based on the risk groups for which the members are classified; and modifying a health care event based on the determined future health care cost.

17. The media claim 16, wherein the set of machine learning algorithms comprises an ensemble of alternating decision trees.

18. The media claim 16, wherein the set of machine learning algorithms comprises a cost-sensitive classifier.

\* \* \* \* \*